US009026216B2

(12) United States Patent
Rossi et al.

(10) Patent No.: US 9,026,216 B2
(45) Date of Patent: May 5, 2015

(54) APPARATUS FOR THE CONTROLLED PRESCRIPTION AND ADMINISTRATION OF TRANSCRANIAL DIRECT CURRENT STIMULATION TREATMENTS IN HUMANS

(76) Inventors: Lorenzo Rossi, Trento (IT); Sara Renata Francesca Marceglia, San Donato Milanese (IT); Simona Mrakic-Sposta, Milan (IT); Laura Bertolasi, Virgilio (IT)

( * ) Notice: Subject to any disclaimer, the term of this patent is extended or adjusted under 35 U.S.C. 154(b) by 447 days.

(21) Appl. No.: 12/997,289

(22) PCT Filed: Jun. 10, 2009

(86) PCT No.: PCT/IT2009/000252
§ 371 (c)(1),
(2), (4) Date: Jan. 28, 2011

(87) PCT Pub. No.: WO2009/150687
PCT Pub. Date: Dec. 17, 2009

(65) Prior Publication Data
US 2011/0118809 A1 May 19, 2011

(30) Foreign Application Priority Data

Jun. 12, 2008 (IT) .............................. MI2008A1064

(51) Int. Cl.
*A61N 1/00* (2006.01)
*A61N 1/08* (2006.01)
(Continued)

(52) U.S. Cl.
CPC ... *A61N 1/08* (2013.01); *A61N 1/05* (2013.01); *A61N 1/37264* (2013.01); *A61N 1/37282* (2013.01)

(58) Field of Classification Search
CPC ..... A61N 1/08; A61N 1/372; A61N 1/37264; A61N 1/37282
See application file for complete search history.

(56) References Cited

U.S. PATENT DOCUMENTS 6,662,052 B1 12/2003 Sarwal et al.
7,460,910 B2 12/2008 Webb
(Continued)

FOREIGN PATENT DOCUMENTS

GB 2435834 A 9/2007
WO 8707511 A2 12/1987
(Continued)

OTHER PUBLICATIONS

Antal, et al., "Homeostatic Metaplasticity of the Motor Cortex is Altered During Headache-Free Intervals in Migraine With Aura", Cerebral Cortex, Nov. 2008, pp. 2701-2705.
(Continued)

*Primary Examiner* — Christopher D Koharski
*Assistant Examiner* — Elizabeth K So
(74) *Attorney, Agent, or Firm* — Pearne & Gordon LLP

(57) ABSTRACT

The invention proposes a system and a method for controlling the process of prescription and administration of direct current stimulation treatments in humans. In the proposed system, the stimulation parameters are all set by a specialist whose credentials are verified through a specific control device different from the device that delivers electrical stimulation. The stimulating device can deliver the stimulation only if the credentials of the specialized subject making the prescription are verified and if the prescription is made according to safety criteria. The system is composed by at least one device for the administration of electrical current connected to two electrodes applied over the skin and by a control device. The control device is connected to one or more devices for the administration of the direct current through a communication channel. The specialist gives his own credentials and is authorized at making the prescription and, accordingly, programming the stimulating device. The prescription defines the stimulus intensity, waveform, polarity, duration, the minimum interval between two consecutive stimulations and the maximum number of stimulations allowed. The stimulating device delivers the stimulation only if the credentials of the specialist are verified and only according to the prescription.

21 Claims, 3 Drawing Sheets

(51) Int. Cl.
*A61N 1/372* (2006.01)
*A61N 1/05* (2006.01)

(56) References Cited

U.S. PATENT DOCUMENTS

| | | | |
|---|---|---|---|
| 7,801,611 | B2 | 9/2010 | Persen et al. |
| 2002/0123673 | A1 | 9/2002 | Webb et al. |
| 2004/0138711 | A1* | 7/2004 | Osorio et al. ............ 607/3 |
| 2005/0131493 | A1 | 6/2005 | Boveja et al. |
| 2005/0182455 | A1 | 8/2005 | Thrope et al. |
| 2005/0288736 | A1 | 12/2005 | Persen et al. |
| 2006/0074465 | A1 | 4/2006 | Webb |
| 2006/0189854 | A1 | 8/2006 | Webb et al. |
| 2007/0032836 | A1 | 2/2007 | Thrope et al. |
| 2007/0032837 | A1 | 2/2007 | Thrope et al. |
| 2007/0191912 | A1* | 8/2007 | Fischer et al. .......... 607/60 |
| 2008/0244717 | A1 | 10/2008 | Jelatis et al. |
| 2009/0054948 | A1 | 2/2009 | Webb |
| 2009/0222058 | A1 | 9/2009 | Craggs |

FOREIGN PATENT DOCUMENTS

| | | | |
|---|---|---|---|
| WO | 2005120637 | A | 12/2005 |
| WO | 2006010166 | A2 | 1/2006 |

OTHER PUBLICATIONS

Antal A, et al., "Transcranial Direct Current Stimulation and Visual Perception", Perception, 2008, vol. 37, pp. 367-374.

Ardolino, et al., "Non-Synaptic Mechanisms Underlie the After-Effects of Cathodal Transcutaneous Direct Current Stimulation of the Human Brain", The Physiological Society, 2005, vol. 568, pp. 653-663, 307, 605, 283.

Boggio, et al., "Effects of Transcranial Direct Current Stimulation on Working Memory in Patients With Parkinson's Disease", Journal of the Neurological Sciences, Elsevier, 2006, vol. 249, pp. 31-38.

Boggio, et al., "Repeated Sessions of Noninvasive Brain DC Stimulation is Associated With Motor Function Improvement in Stroke Patients", Restorative Neurology and Neuroscience, 2007, vol. 25, pp. 123-129.

Cogiamanian, et al., "Improved Isometric Force Endurance After Transcranial Direct Current Stimulation Over the Human Motor Cortical Areas", European Journal of Neuroscience, 2007, vol. 26, pp. 242-249.

Fecteau, et al. "Activation of Prefrontal Cortex by Transcranial Direct Current Stimulation Reduces Appetite for Risk During Ambiguous Decision Making", Journal of Neuroscience, 2007, vol. 27, pp. 6212-6218.

Ferrucci, et al., "Transcranial Direct Current Stimulation Improves Recognition Memory in Alzheimer Disease", Neurology, AAN Enterprises, 2008, pp. 1-6

Ferrucci, et al., "Cerebellar Transcranial Direct Current Stimulation Impairs the Practice-Dependent Proficiency Increase in Working Memory", Journal of Cognitive Neuroscience, 2008, vol. 20, Issue 9, pp. 1687-1697.

Fregni, et al., "Cortical Stimulation of the Prefrontal Cortex With Transcranial Direct Current Stimulation Reduces Cue-Provoked Smoking Craving: A Randomized, Sham-Controlled Study", Journal of Clinical Psychiatry, 2007, vol. 68, pp. 1-9.

Fregni, et al., "Transcranial Direct Current Stimulation of the Prefrontal Cortex Modulates the Desire for Specific Foods", Appetite, 2008, vol. 51, pp. 34-41.

Lang, et al, "Preconditioning With Transcranial Direct Current Stimulation Sensitizes the Motor Cortex to Rapid-Rate Transcranial Magnetic Stimulation and Controls the Direction of After-Effects", Biological Psychiatry, 2004, vol. 56, pp. 634-639.

Liebetanz, et al., "Pharmacological Approach to the Mechanisms of Transcranial DC-Stimulation-Induced After-Effects of Human Motor Cortex Excitability", Brain 2002, vol. 125, pp. 2238-2247.

Monti, et al., "Improved Naming After Transcranial Direct Current Stimulation in Aphasia", Journal Neurological Neurosurgical Psychiatry, 2008, vol. 79, pp. 451-453.

Mrakic-Sposta, et al., "Decreased Motor Tics After Transcranial Direct Current Stimulation (TDCS) Over the Frontal Lobes in a Patient With Tourette Syndrome", Neurological Science 2007, vol. 28, pp. 282.

Nitsche, et al., "Modulation of Cortical Excitability by Transcranial Direct Current Stimulation", Nervenarzt 2002; 73: 332-5.; English abstract is attached.

Nitsche, et al., "Safety Criteria for Transcranial Direct Current Stimulation (TDCS) in Humans", Clinical Neurophysiology, Elsevier Science Ireland Ltd., 2003, vol. 114, pp. 2220-2223.

Nitsche, et al., "Dopaminergic Modulation of Long-Lasting Direct Current-Induced Cortical Excitability Changes in the Human Motor Cortex", European Journal of Neuroscience, Federation of European Neuroscience and Blackwell Publishing Ltd., 2006, vol. 23, pp. 1651-1657.

Priori, A. "Brain Polarization in Humans: A Reappraisal of an Old Tool for Prolonged Non-Invasive Modulation of Brain Excitability", Clinical Neurophysiology, Elsevier Science Ireland Ltd., 2003, vol. 114, pp. 589-595.

Priori, et al., "Lie-Specific Involvement of Dorsolateral Prefrontal Cortex in Deception", Cerebral Cortex Jul. 2008, Oxford University Press, vol. 18, pp. 451-455.

Quartarone, et al., "Motor Cortex Abnormalities in Amyotrophic Lateral Sclerosis With Transcranial Direct-Current Stimulation", Muscle & Nerve, Wiley Periodicals, Inc., May 2007, vol. 35, pp. 620-624.

Wu et al., "Noninvasive Brain Stimulation for Parkinson'S Disease and Dystonia", Neurotherapeutics, The Journal of the American Society for Experimental Neurotherapeutics, Apr. 2008, vol. 5, pp. 345-361.

* cited by examiner

APPARATUS FOR THE CONTROLLED PRESCRIPTION AND ADMINISTRATION OF TRANSCRANIAL DIRECT CURRENT STIMULATION TREATMENTS IN HUMANS

TECHNICAL FIELD

This invention describes a system able to control the process of prescription and administration of electrical stimulation treatments in humans. In the described system, the credentials for the authentication of the specialized subject making the prescription are verified by the system itself. The system is composed by two sub-systems: the first one is for the administration of the treatment by delivering electric currents to the human body; the second one is for checking the credentials of the specialists who are authorized to set stimulation parameters through a prescription. The credential check is a process that verifies the identity of the subject through an authentication method, such as alpha-numeric keys known by the subject, or biometric features, or objects that the subject has (smart cards) authorized for identity recognition, or any combination of these three methods. "Prescription" is the definition of a finite number of electrical stimulations with a given time length and given stimulation characteristics.

BACKGROUND

Transcranial direct current stimulation is a neurophysiological technique able to modulate the excitability of the biological tissue of the central and peripheral nervous system, through the delivery, for a finite time length, of an electrical field generating a current flow and a net relative electrical charge passing through the biological tissue itself (Priori et al, 2003). The difference between direct current stimulation and other electrical stimulations is the presence of this net positive charge passing through the tissue and obtained through mono-directional currents, called "direct currents". Physical and biochemical mechanisms induced in the nervous tissue by the administration of direct currents are not yet completely clear (Ardolino et al, 2005). Several studies (Lang et al, 2004; Nitsche et al, 2006) hypothesize that the application of constant electrical fields for a certain amount of time induce electrochemical mechanisms producing the excitation or inhibition of the nervous tissue also through the activation of the second-messenger system, and generating effects lasting also for some weeks (Liebetanz et al, 2002; Nietsche et al, 2002). Direct current stimulation is applied through a current generator connected to a pair (or more) electrodes applied on the skin, soaked with a saline solution, so that the electrical charge can be transmitted to the tissue. There usually are two electrodes, the first one, known as the "active" electrode, is placed over the part of the tissue that should be treated, the second one is the "reference" electrode. Different applications have different electrode montages. The type of treatment refers to the polarity of the active electrode respect to the reference electrode: if the electric potential of the active electrode is higher than that of the reference electrode, the treatment is called "anodal", otherwise it is "cathodal". In some particular cases, more active electrodes are placed on the scalp to treat symmetric brain regions, and only one reference electrode is used to guarantee the correct current flow. Current density, defined as the ratio between the electrical current to the tissue and the area of the active electrode, is usually between 0.01 and 0.5 $mA/cm^2$.is. For instance, a 30 $cm^2$ electrode can deliver currents ranging from 1 to 5 mA. The duration of the treatment ranges from 10 to 30 minutes. The net charge to the human body is calculated as the time integral of the electrical current applied. The impedance on the current generator is mainly due to the resistance of the electrodes that are, therefore, kept wet though saline solutions and conductive gels. To ensure safety, the system do not apply potential differences above 30 V, thus limiting the current delivered in the case of excessive load increase. The treatments applied do not exceed one administration per day and for a limited number of days. At present, direct current stimulation has been recognized as an effective adjuvant treatment for several neurological and neuropsychiatric diseases, such as Alzheimer disease, Parkinson's disease, post-stroke aphasia, lateral amyotrophic sclerosis, ictus, dystonia, headache, Tourette syndrome (Antal et al, 2008; Boggio et al, 2006; Boggio et al, 2007; Ferrucci et al, 2008a; Monti et al, 2008; Mrakic-Sposta et al, 2008; Quartarone et al, 2007; Wu et al, 2008). In addition, direct current stimulation is under study for the treatment of other pathologies and for the modulation of particular behaviors in normal subjects (Antal and Paulus, 2008). Some applications of the technique have been proposed also for the control of muscular fatigue (Cogiamanian et al, 2007), showing an increase of 20% of endurance time, and also for the modulation of deception processes (Priori et al, 2008), of moral choices, and for enhancing learning and decision making processes (Fecteau et al, 2007; Ferrucci et al, 2008b; Fregni et al, 2008a; Fregni et al, 2008b). Safety and efficacy of the treatment depend on a correct administration, that should be properly tested and verified (Nietsche et al, 2003). Conversely, if the treatment is administered through a wrong montage, and, moreover, through wrong stimulation intensities, or frequency of application, adverse effects cannot be excluded. Hence, direct current stimulation could be potentially dangerous if the subject is left free to administer the treatment by himself, as well as in the case of the administration of particular active pharmacological principles. For this reason, at present, systems for direct current stimulations are given only to specialized personnel, who are authorized to administer the treatment to patients in specific clinical areas, verifying the frequency of administration, stimulation parameters, and electrode montages. This, however, limits the range of possible application of the direct current stimulation. Because the treatment can be delivered only in specialized clinical centers and because it has to be done for a number of consecutive days, the associated costs (personnel, subjects' hospitalization, transport or housing of subjects who must reach the specialized centers for some consecutive days, and costs deriving from the inability of the treated subject to make his own activities) are a limitation for the widespread diffusion of the treatment. Conversely, an application that is controlled by specialized personnel but delivered by the patient himself at home could increase the efficacy of this methodology thus enhancing its applicability and diffusion.

DISCLOSURE OF INVENTION

The object of this invention is a system for controlling the administration of direct current stimulation treatments in humans also in the domestic environment and without the presence of specialized personnel. As previously described, in fact, the treatment could produce damages if not administered with proper pathophysiological indications and with frequencies and intensities not responding to specific criteria. Electrode montage could be more easily controlled through the application of pre-cabled helmets or caps with a precise location of the electrodes. The use of conventional programmable direct current stimulators do not ensure patient's safety. In fact, in traditional programmable stimulators only stimulation parameters can be set, whereas nor the number of daily applications nor the total number of treatments can be set, thus enabling a continue, and uncontrolled use of the system. The first innovative feature of the invention is the merging of the concept of therapeutic prescription with the programming procedure of an electrical stimulator. As well as therapeutic prescription are given for a limited amount of time, the proposed system allows only a finite number of applications after which the system is inactive and cannot deliver any other stimulation. Only after the setting of a new prescription made by specialized personnel the apparatus will deliver again electrical stimulations. The prescription, or the setting of the stimulator, should be done only by specialized personnel, authorized by an authentication process. The second innovative feature of the present invention is the process of credential testing and verification for the subject that is prescribing the treatment that is done by an apparatus different from the apparatus delivering the stimulation. In fact, in traditional stimulators, parameters can be set after the recognition of a security code, with the authentication process directly implemented on the stimulating system. There are different scenarios for the application of this authentication model (directly implemented on the stimulating device) that, however, have several limitations for its widespread diffusion. A first scenario is that of a single device with a single security code, also re-programmable. The most important limitation of such a scenario is due to the possibility, for who owns the system, to program the code, thus being free to use the system inappropriately. Conversely, if the device is given to the patient by the authorized subject without giving the code associated to the device, the patient will not be able to go to another specialist for re-programming the device. In a second scenario, a finite set of login credentials (or a method for the automatic generation of credentials) is stored on the device when manufactured. However, this procedure cannot be considered safe. A distribution to the public of devices containing all the credentials (or the method for their generation) increases the possibility of cracking the system and extracting these credentials, thus making all the devices possibly unsafe. The present invention proposes a method for credential verification on an external control device, thus implementing a safe method also for widespread diffusion. The external control device is connected to the stimulating devices through a communicating channel also supposed unsafe. The control device should receive the credentials of the subject that will make the prescription, whereas the stimulating device should receive both the prescription and the notification of the positive result of the credential verification process. In this case, and only in this case, the stimulating device will set the stimulation parameters according to the prescription received and is enabled for the treatment administration. There are different possible ways of interaction between the subject making the prescription and the different stimulating devices. Other features and advantages of this invention will be better detailed when the best mode (which is not the only mode) of carrying out the invention will be presented. In the next sections, a brief description of the drawings that represent the best mode of carrying out the invention will be given. Note that the drawings have only a descriptive aim and do not limit the modes in which the invention could be realized.

BEST MODE OF CARRYING OUT THE INVENTION

Figure 1:
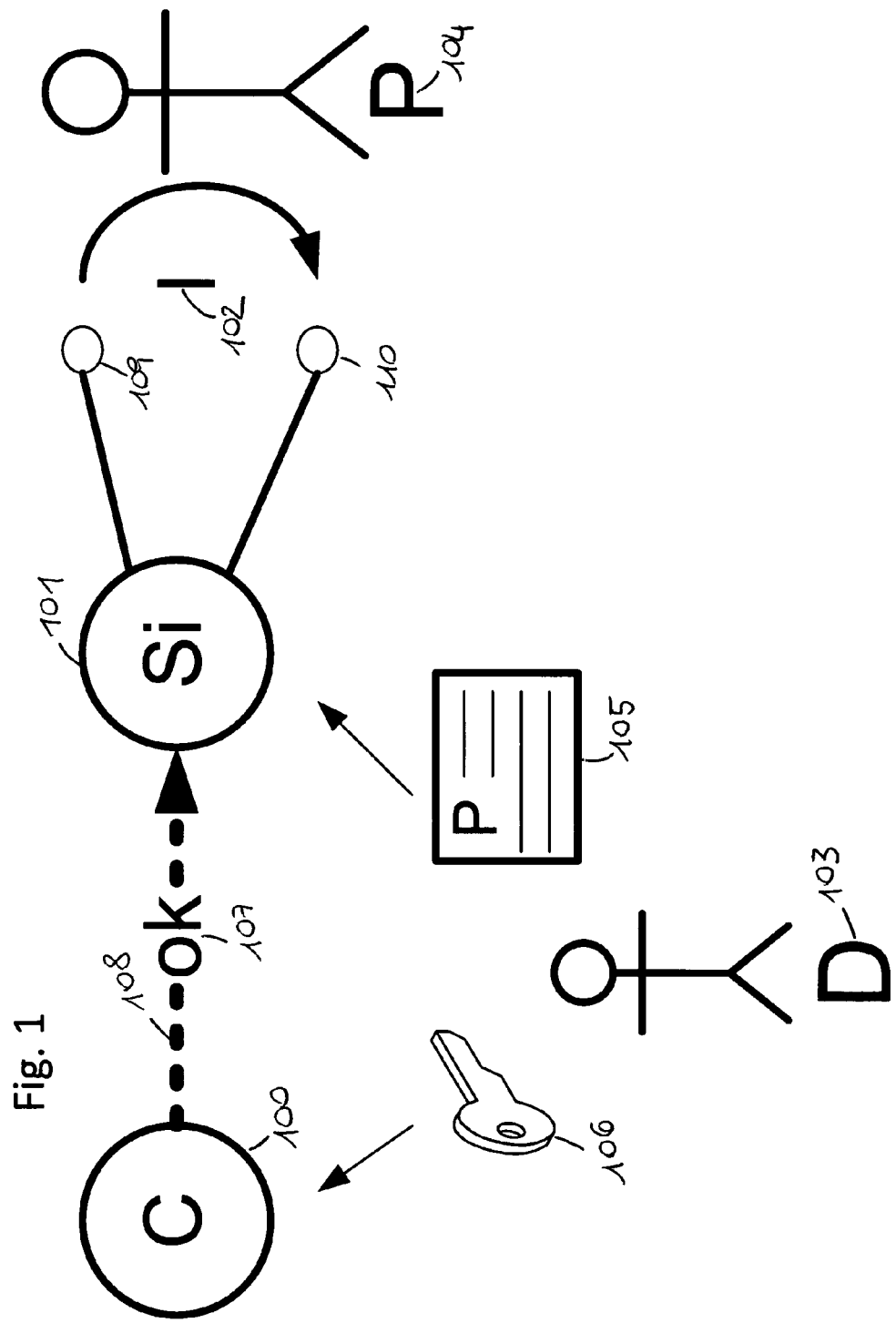
FIG. 1 shows the architecture of the system for controlling the process of prescription and administration of direct current stimulation treatments in humans, according to the proposed invention.
Figure 2:
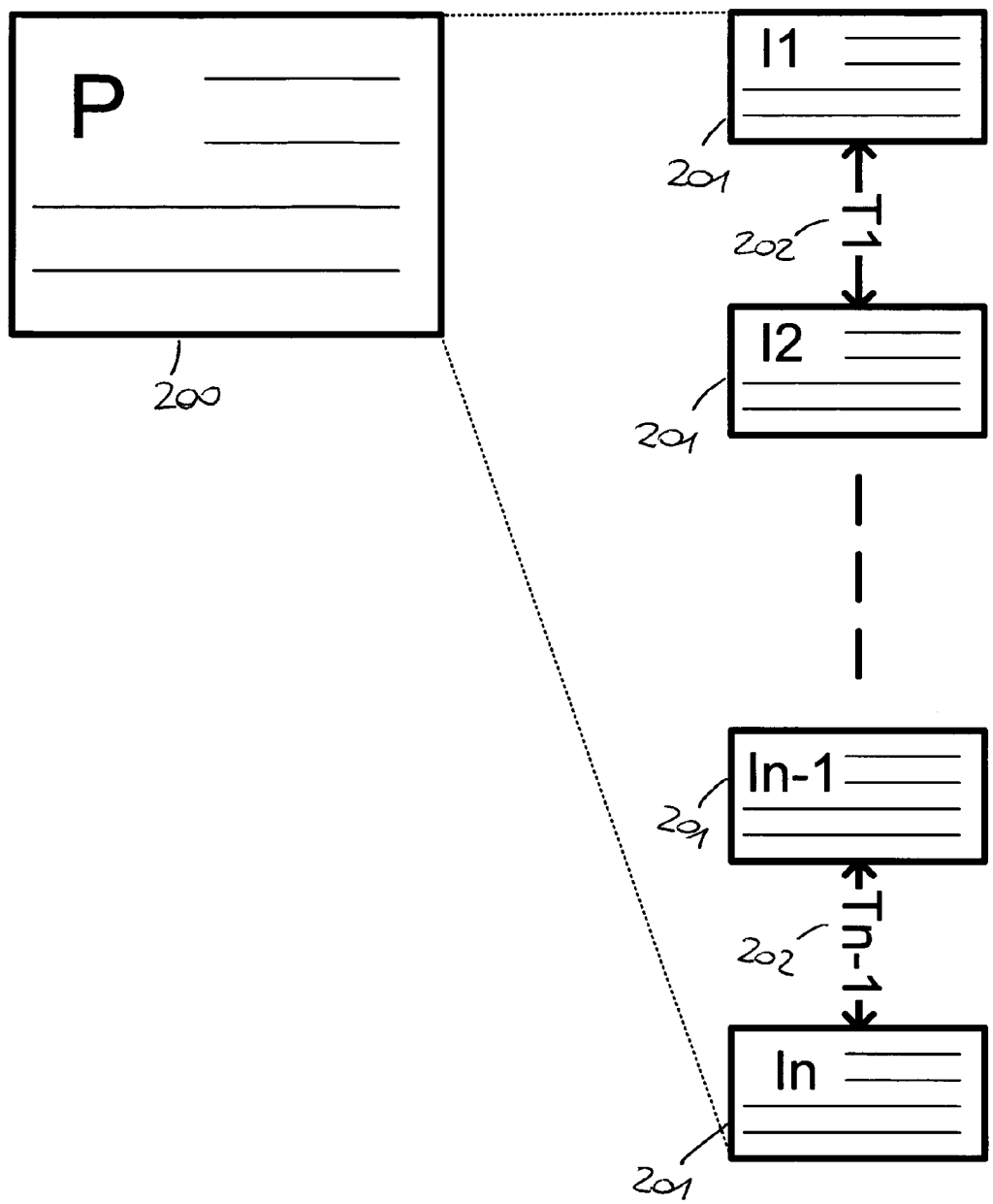
FIG. 2 shows the logic structure of the prescription that defines a stimulating treatment according to the proposed invention.
Figure 3:
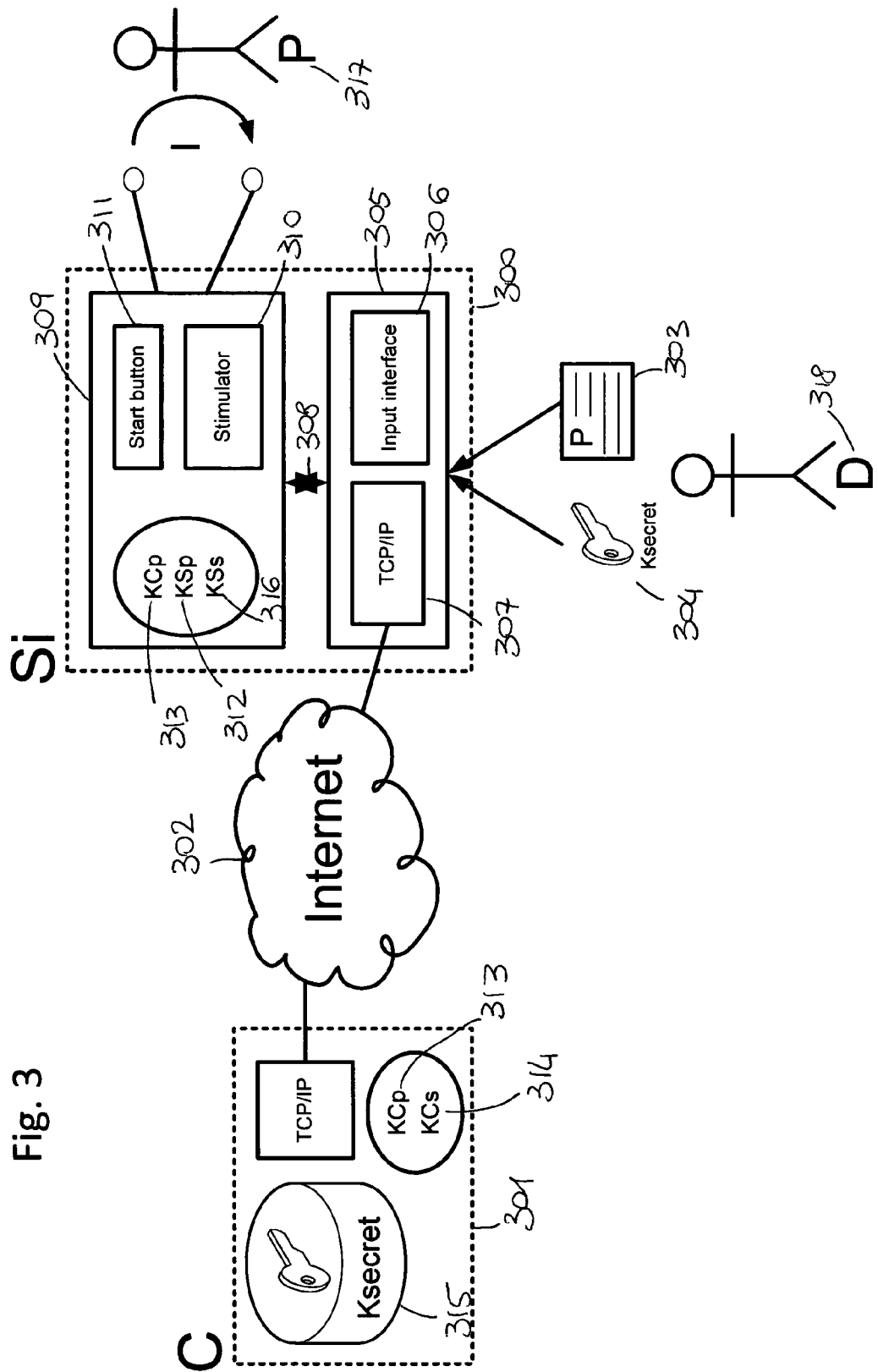
FIG. 3 shows a possible implementation of the system for controlling the process of prescription and administration of direct current stimulation treatments in humans, according to the proposed invention.

In particular, the system drawn in FIG. 1 can control the process of prescription and administration of direct current stimulation treatments in humans, according to the proposed invention. As in FIG. 1, the system is composed by a control device (100), by one or more devices (101) for the administration of the direct current stimulation treatment (102). There are two users, one is the subject that is authorized to make the prescription of the direct current stimulation treatment (103), and the other one is the subject receiving the treatment (104). The treatment is prescribed by the subject authorized (103) who inserts a prescription (105) through a generic input device. Together with the prescription, in the system are also inserted the credentials for authentication (106) that are verified by the control device (100) that sends the result of the authentication process (107) to the stimulating device (101) through a generic communication channel, also supposed unsafe (108). The stimulating device (101) administers to the patient (104) the direct current stimulation treatment (102) only if the result of the authentication process, carried out by the control device (100), is positive (107). The stimulating device (101) delivers a direct current according to the parameters indicated in the prescription (105) to the subject (104) through at least two electrodes (109-110). As shown in FIG. 2, the prescription of the treatment (200) is defined by a finite set of stimulations (201), with a defined time interval elapsing between two consecutive stimulations (202) that prevents from excessive use. Each stimulation (201) is defined by parameters such as stimulus intensity, stimulus waveform (constant current or randomized current with a given mean value), stimulus polarity (anodal, cathodal, or sham), stimulation duration. The minimum time interval (202) elapsing between two consecutive stimulations can be directly defined either indicating the number of treatments per day/week/month, or indicating the dates on a calendar. Stimulation parameters that can be set cannot exceed safety indications for total net charge delivered to the tissue. Prescriptions exceeding those safety limits cannot be prescribed. In FIG. 3 is shown a possible technological implementation that is considered the best mode to carry out the invention (from here called best configuration), but it does not exclude other possible implementations. In such solution, the stimulating device (300) and the control device (301) are connected through the Internet (302) using the TCP/IP telecommunication standard.

The stimulating device (300) receives the prescription (303) and an alphanumeric code (304), called Ksecret, through an input device (305), that, in the best configuration, is a touch screen monitor inserted in a dedicated module (306) of the stimulating device (300) together with the telecommunication interface TCP/IP (307). In this way, the subject who makes the prescription has a module (306) interfaced through a dedicated cable (308) to another module (309) including a programmable stimulator (310) and a patient interface (311). In the best configuration, the stimulating device (300) includes two modules, connected through a dedicated cable (308), one containing the technology for stimulus delivery (309), and the other one (306) representing the interface between the device (300) and both the subject making the prescription (318) and the technology for data transmission (302). Each interface module (306) can be connected to one or more stimulation modules (309) thus limiting the costs for a single stimulating device (300). The stimulating device (300) receives the prescription (303), as defined in FIG. 2, and the Ksecret alpha-numeric code (304), that represent the credentials of the subject making the prescription (318). The stimulating device encrypts the alpha-numeric code (304) received with the prescription and its public key (312) with the public key (313) of the control device (301) directly stored on the device itself when manufactured. The encrypted package is sent to the control device (301), converted to the standard TCP/IP and sent to the IP address where the control device (301) can be found. The control device (301) is implemented through a server that receives the TCP/IP package, extracts the encrypted data in the package, and decrypts the package sent by the stimulating device (300) through its secret key (314). After decrypting the received package, the credentials (304) of the subject making the prescription (318) are obtained and verified by querying a knowledge base (315) that contains all the active credentials. The result of the verification process is encrypted through the public key (312) of the stimulating device (300) obtained after decrypting the package received. The result of the verification process is sent through the Internet (302) following the TCP/IP protocol to the stimulating device (300). The stimulating device (300) decrypts the received data through its private key (316) and checks the result of the authentication process before programming the stimulation according to the prescription received. The stimulating device (300) is then programmed and ready for the administration of the treatment. In the best configuration, the subject who receives the treatment (317) connects the module for treatment administration (309) to the electrodes in a montage defined by a dedicated cap or helmet, and starts the treatment through a start button (311) on the stimulating device (300). The module for treatment administration (309) verifies that the stimulation delivered is correct (according to the prescription) monitoring the difference of electrical potential between the two electrodes and through an internal counter that, in the best configuration, is implemented through a real time watch, delivering the stimulation for the fixed amount of time. Once the stimulation ended, the stimulating device (300) remains inactive until the fixed interval between two consecutive stimulations (202) is fully elapsed. Hence, if the subject receiving the treatment (317) tries to push again the start button (311) to make an unscheduled stimulation before the interval is elapsed, the module for treatment administration (309) do not deliver any current. In the best configuration, the control device (301) is managed by a third subject, here generically indicated as the "manufacturer", who defines the guidelines for the accreditation of subjects to the prescription of stimulation treatments, according to the national law or under scientific recommendations, and has the due to keep these guidelines secret to ensure the general safety of the control system described in the present invention.

REFERENCES

Antal A, Lang N, Boros K, Nitsche M, Siebner H R, Paulus W. Homeostatic Metaplasticity of the Motor Cortex is Altered during Headache-Free Intervals in Migraine with Aura. Cereb Cortex 2008.
Antal A, Paulus W. Transcranial direct current stimulation and visual perception. Perception 2008; 37: 367-74.
Ardolino G, Bossi B, Barbieri S, Priori A. Non-synaptic mechanisms underlie the after-effects of cathodal transcutaneous direct current stimulation of the human brain. J Physiol 2005; 568: 653-63.
Boggio P S, Ferrucci R, Rigonatti S P, Covre P, Nitsche M, Pascual-Leone A, et al. Effects of transcranial direct current stimulation on working memory in patients with Parkinson's disease. J Neurol Sci 2006; 249: 31-8.
Boggio P S, Nunes A, Rigonatti S P, Nitsche M A, Pascual-Leone A, Fregni F. Repeated sessions of noninvasive brain DC stimulation is associated with motor function improvement in stroke patients. Restor Neurol Neurosci 2007; 25: 123-9.
Cogiamanian F, Marceglia S, Ardolino G, Barbieri S, Priori A. Improved isometric force endurance after transcranial direct current stimulation over the human motor cortical areas. Eur J Neurosci 2007; 26: 242-9.
Fecteau S, Pascual-Leone A, Zald D H, Liguori P, Theoret H, Boggio P S, et al. Activation of prefrontal cortex by transcranial direct current stimulation reduces appetite for risk during ambiguous decision making. J Neurosci 2007; 27: 6212-8.
Ferrucci R, Mameli F, Guidi I, Mrakic-Sposta S, Vergari M, Marceglia S, et al. Transcranial direct current stimulation improves recognition memory in Alzheimer disease. Neurology 2008a.
Ferrucci R, Marceglia S, Vergari M, Cogiamanian F, Mrakic-Sposta S, Mameli F, et al. Cerebellar Transcranial Direct Current Stimulation Impairs the Practice-dependent Proficiency Increase in Working Memory. J Cogn Neurosci 2008b.
Fregni F, Liguori P, Fecteau S, Nitsche M A, Pascual-Leone A, Boggio P S. Cortical stimulation of the prefrontal cortex with transcranial direct current stimulation reduces cue-provoked smoking craving: a randomized, sham-controlled study. J Clin Psychiatry 2008a; 69: 32-40.
Fregni F, Orsati F, Pedrosa W, Fecteau S, Tome F A, Nitsche M A, et al. Transcranial direct current stimulation of the prefrontal cortex modulates the desire for specific foods. Appetite 2008b; 51: 34-41.
Lang N, Siebner H R, Ernst D, Nitsche M A, Paulus W, Lemon R N, et al. Preconditioning with transcranial direct current stimulation sensitizes the motor cortex to rapid-rate transcranial magnetic stimulation and controls the direction of after-effects. Biol Psychiatry 2004; 56: 634-9.
Liebetanz D, Nitsche M A, Tergau F, Paulus W. Pharmacological approach to the mechanisms of transcranial DC-stimulation-induced after-effects of human motor cortex excitability. Brain 2002; 125: 2238-47.
Monti A, Cogiamanian F, Marceglia S, Ferrucci R, Mameli F, Mrakic-Sposta S, et al. Improved naming after transcranial direct current stimulation in aphasia. J Neurol Neurosurg Psychiatry 2008; 79: 451-3.
Mrakic-Sposta S, Mameli F, Ferrucci R, Dilena R, Marceglia S, Vergari M, et al. Decreased motor tics after transcranial direct current stimulation (tDCS) over the frontal lobes in a patient with Tourette syndrome. Neurol Sci 2007; 28: 282.
Nitsche M A, Lampe C, Antal A, Liebetanz D, Lang N, Tergau F, et al. Dopaminergic modulation of long-lasting direct current-induced cortical excitability changes in the human motor cortex. Eur J Neurosci 2006; 23: 1651-7.
Nitsche M A, Liebetanz D, Lang N, Antal A, Tergau F, Paulus W. Safety criteria for transcranial direct current stimulation (tDCS) in humans. Clin Neurophysiol 2003; 114: 2220-2; author reply 2222-3.

Nitsche M A, Liebetanz D, Tergau F, Paulus W. [Modulation of cortical excitability by transcranial direct current stimulation]. Nervenarzt 2002; 73: 332-5.

Priori A. Brain polarization in humans: a reappraisal of an old tool for prolonged non-invasive modulation of brain excitability. Clin Neurophysiol 2003; 114: 589-95.

Priori A, Mameli F, Cogiamanian F, Marceglia S, Tiriticco M, Mrakic-Sposta S, et al. Lie-specific involvement of dorsolateral prefrontal cortex in deception. Cereb Cortex 2008; 18: 451-5.

Quartarone A, Lang N, Rizzo V, Bagnato S, Morgante F, Sant'angelo A, et al. Motor cortex abnormalities in amyotrophic lateral sclerosis with transcranial direct-current stimulation. Muscle Nerve 2007; 35: 620-4.

Wu A D, Fregni F, Simon D K, Deblieck C, Pascual-Leone A. Noninvasive brain stimulation for Parkinson's disease and dystonia. Neurotherapeutics 2008; 5: 345-61.

The invention claimed is:

1. A system to control the process of prescription and administration of electrical direct current stimulation treatments for neuromodulation of nervous tissue, the system comprising:
   a. at least two electrodes adapted to be applied externally on the skin of a subject;
   b. at least one stimulating device adapted to be provided externally to the subject for administration of electrical current stimulation treatment, wherein the at least one stimulating device is connected to the at least two electrodes;
   c. a control device connected to the at least one stimulating device through an unsafe communication channel;
wherein the at least one stimulating device is enabled by said subject to stimulation treatment delivery only according to modalities defined in a prescription made by a specialized subject and only after having received from the control device a positive result of a verification of a credential of the specialized subject who is making the prescription, wherein the prescription is defined as a finite number of stimulations with a specific minimum time interval between two consecutive stimulations,
and wherein the at least one stimulating device is not activated by said subject for a new stimulation treatment delivery when the finite number of stimulations is reached for the current stimulation treatment or until the specific minimum time interval between two consecutive stimulation treatments is fully elapsed, thus preventing the subject to make unscheduled stimulation treatments,
and wherein the at least one stimulating device comprises a start button pushed by said subject to start the stimulation, wherein said start button remains inactive until the fixed interval between two consecutive stimulations is fully elapsed.

2. A system as claimed in claim 1, wherein the at least one stimulating device is a pre-cabled helmet or a cap with a precise location of the at least two electrodes.

3. A system as claimed in claim 1, wherein the at least one stimulating device is not enabled to the stimulation treatment delivery without receiving the positive result from a credential verification process carried out by the control device and transmitted through the unsafe communication channel.

4. A system as claimed in claim 1 wherein each stimulation is defined by parameters such as stimulus intensity, stimulus waveform—constant current or randomized current with a given mean value-, stimulus polarity—anodal, cathodal, or sham-, stimulation duration.

5. A system as claimed in claim 1 wherein the minimum time interval elapsing between two consecutive stimulations is directly defined either indicating a number of treatments per day/week/month, or indicating dates on a calendar.

6. A system as claimed in claim 1, wherein the at least one stimulating device includes two modules connected through a dedicated cable, one containing a technology for stimulus delivery and the other one representing an interface between the at least one stimulating device and both the subject making the prescription and a technology for data transmission.

7. A system as claimed in claim 6 further comprising an interface module composed by an input device and by a telecommunication interface TCP/IP.

8. A system as claimed in claim 6, wherein the at least one stimulating device receives the prescription and an alpha-numeric code through an input device.

9. A system as claimed in claim 8 further comprising an input device implemented through a touch screen monitor.

10. A system as claimed in claim 6, wherein the at least one stimulating device further comprises a module for treatment administration including a programmable stimulator and a subject interface.

11. A system as claimed in claim 10 further comprising a subject interface implemented as said start button for activating a prescribed stimulation.

12. A system as claimed in claim 6 further comprising a module for treatment administration that verifies whether the stimulation treatment delivery is correct by monitoring a difference of electrical potential between the two electrodes.

13. A system as claimed in claim 1, wherein the at least one stimulating device and the control device are connected through the unsafe communication channel which is Internet using a TCP/IP telecommunication standard.

14. A system as claimed in claim 1, wherein the control device is implemented through a server that receives data according to a TCP/IP standard and that contains a knowledge base with all active credentials.

15. A system as claimed in claim 14, wherein the at least one stimulating device includes two modules connected through a dedicated cable, one containing a technology for stimulus delivery and the other one representing an interface between the device and both the subject making the prescription and a technology for data transmission, wherein the at least one stimulating device and the control device are connected through Internet using a TCP/IP telecommunication standard wherein data transmission between the control device and the at least one stimulating device is encrypted through a public key system with asymmetric encrypting algorithms.

16. A system as claimed in claim 15, wherein at least a public key of the at least one stimulating device, a private key of the at least one stimulating device and a public key of the control device are stored when the at least one stimulating device is manufactured.

17. A system as claimed in claim 15, wherein the at least one stimulating device encrypts an alpha-numeric code received with the prescription and its public key with a public key of the control device and it transmits an encrypted package to the control device, that decrypts the package through its secret key and sends the result of a verification process encrypted through a public key of the at least one stimulating device to the at least one stimulating device itself that decrypts received data through its private key.

18. A system as claimed in claim 17, wherein the encrypted data packages are converted to the standard TCP/IP and sent to an IP address where the control device can be found.

19. A system as claimed in claim 14, wherein the at least one stimulating device and the control device are connected through Internet using a TCP/IP telecommunication standard and a credential of the subject making the prescription are obtained and verified by querying a knowledge base that contains all active credentials and that is included in the control device.

20. A system as claimed in claim 14, wherein the at least one stimulating device and the control device are connected through Internet using a TCP/IP telecommunication standard and the at least one stimulating device checks a result of an authentication process before programming a stimulation according to the prescription received.

21. A system as claimed in claim 14, wherein the at least one stimulating device and the control device are connected through Internet using a TCP/IP telecommunication standard and the knowledge base where all active credentials are stored and included in the control device is kept secret to the subjects who could receive a stimulation or who could prescribe a treatment.

* * * * *